(12) United States Patent
Norman et al.

(10) Patent No.: US 9,814,845 B1
(45) Date of Patent: Nov. 14, 2017

(54) HEATED PATIENT TUBE ASSEMBLY

(71) Applicants: Scott Norman, Stilwell, KS (US); Mark Petheram, Overland Park, KS (US); Anthony Hash, Olathe, KS (US)

(72) Inventors: Scott Norman, Stilwell, KS (US); Mark Petheram, Overland Park, KS (US); Anthony Hash, Olathe, KS (US)

( * ) Notice: Subject to any disclaimer, the term of this patent is extended or adjusted under 35 U.S.C. 154(b) by 0 days.

(21) Appl. No.: 15/348,187

(22) Filed: Nov. 10, 2016

(51) Int. Cl.
*A61M 5/44* (2006.01)
*A61M 25/00* (2006.01)

(52) U.S. Cl.
CPC .......... *A61M 5/44* (2013.01); *A61M 25/0012* (2013.01); *A61M 2205/3368* (2013.01); *A61M 2205/3584* (2013.01); *A61M 2205/368* (2013.01); *A61M 2205/3653* (2013.01)

(58) Field of Classification Search
CPC ............ A61M 5/44; A61M 2205/3368; A61M 25/0012
See application file for complete search history.

(56) References Cited

U.S. PATENT DOCUMENTS

| | | | |
|---|---|---|---|
| 4,038,519 A * | 7/1977 | Foucras ................ | A61M 1/369 138/133 |
| 5,100,388 A * | 3/1992 | Behl .................... | A61B 18/082 604/113 |
| 2008/0159726 A1* | 7/2008 | Barkey .................... | H05B 3/78 392/489 |

* cited by examiner

*Primary Examiner* — Nathan R Price
*Assistant Examiner* — Anh Bui
(74) *Attorney, Agent, or Firm* — Hovey Williams LLP

(57) ABSTRACT

A heated patient tube assembly that carries and gradually warms fluids to a desired temperature and maintains the desired temperature until the fluids are delivered to a patient includes an elongated hollow tube; a heating assembly at least partially embedded within the tube for heating the tube and fluids carried in the tube; and a control assembly for controlling the heating assembly such that the fluids exit the tube at a desired and consistent temperature.

8 Claims, 6 Drawing Sheets

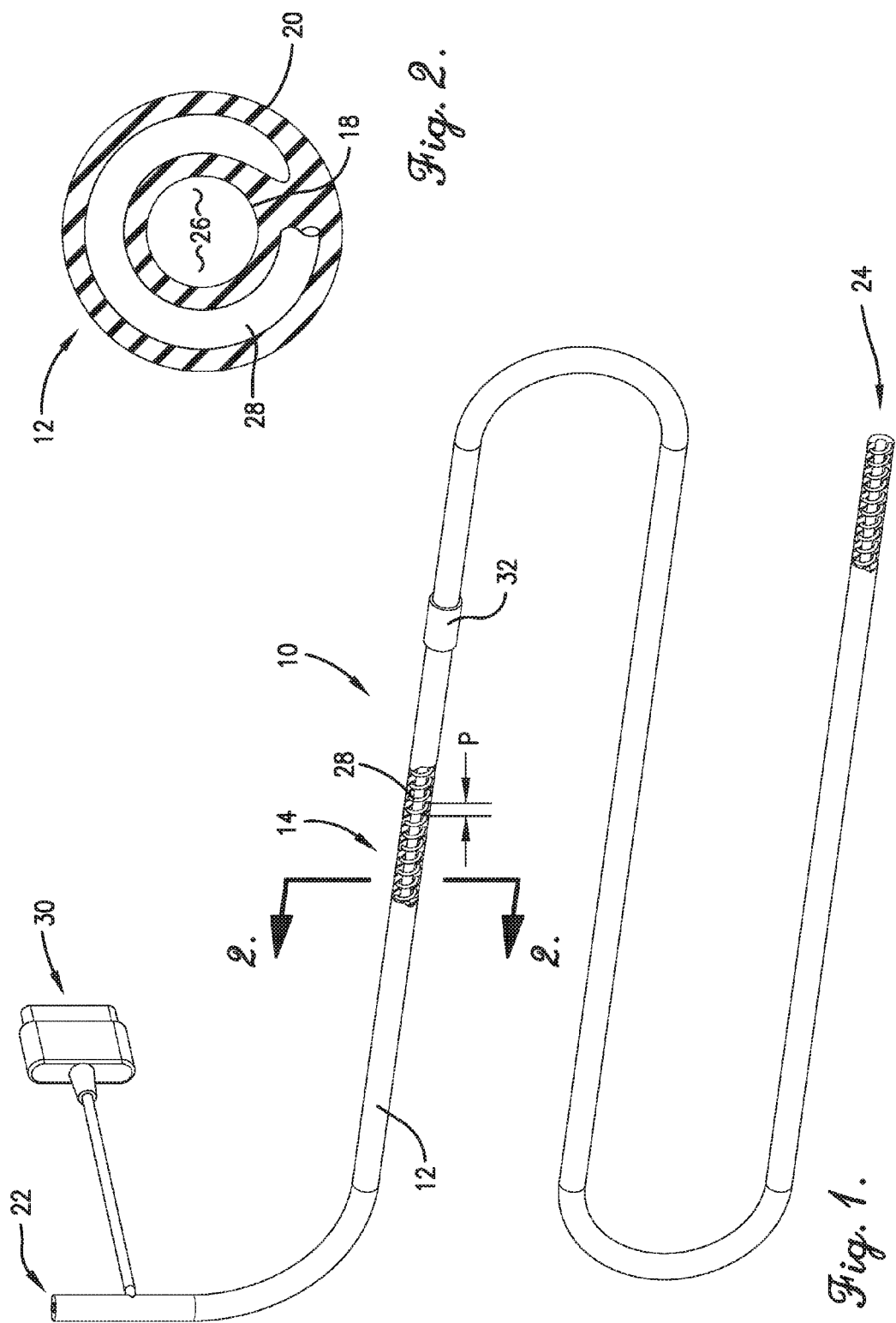

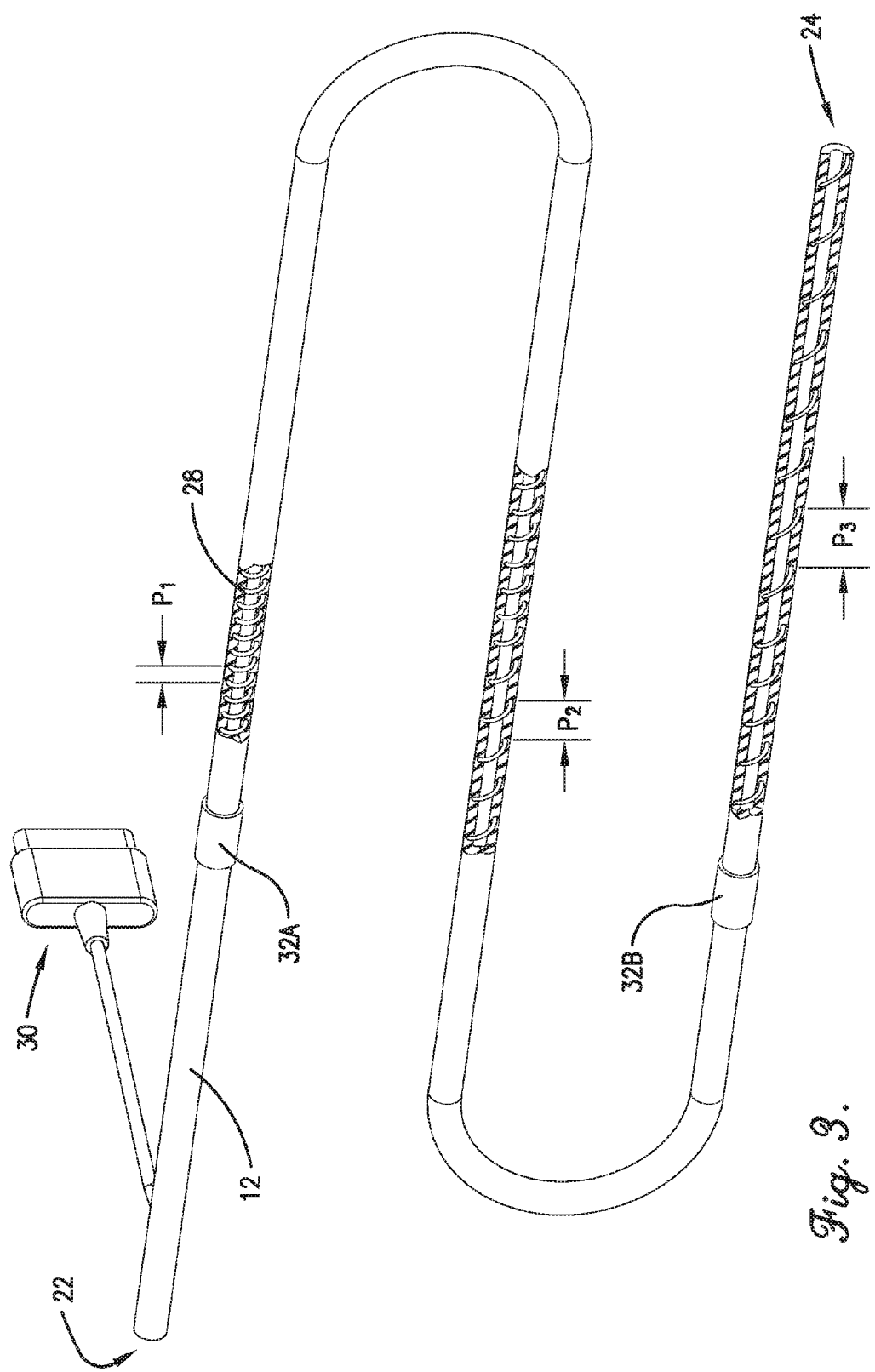

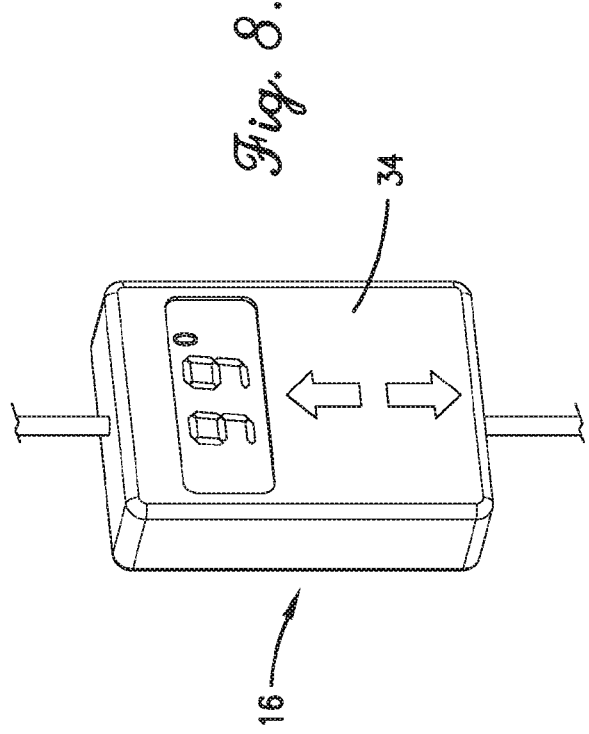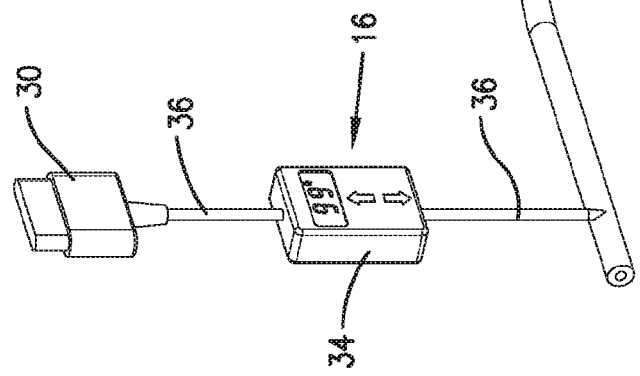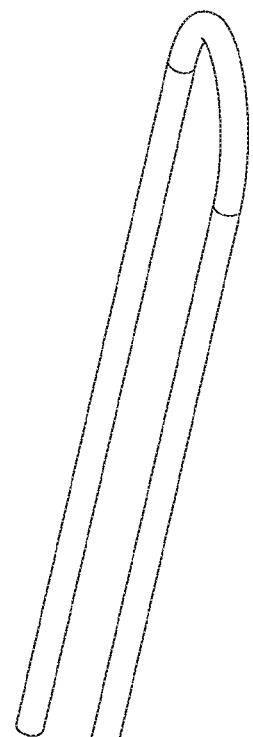

HEATED PATIENT TUBE ASSEMBLY

BACKGROUND

Intravenous (IV) tubes, enteral feeding tubes, blood transfusion tubes, and other fluid-carrying tubes are often used to deliver IV fluids, milk, feeding formulas, blood, and other fluids to infants, elderly person, and other patients. Because these fluids are often collected in advance and refrigerated, they must be warmed before given to patients.

Fluid warming devices have been developed for this purpose. One conventional type of fluid warming device has one or more heated wells or chambers in which fluid storage bags are placed to heat the fluids in the bags before the fluids are provided to patients. Another type of fluid warming device includes a heated enclosure through which a fluid tube is threaded so that fluids in the tube are heated as they pass through the heated enclosure.

Both of the above-described types of fluid warming devices are often ineffective because they fail to maintain the temperature of fluids after the fluids exit the devices. To compensate for such temperature drops, the warming devices must heat the fluids to higher than needed temperatures. But unnecessarily high temperatures may negatively break down nutrients and medication properties in the fluids and may damage the tubes and introduce foreign particles from the tubes into the fluids. Higher heating temperatures can also deliver fluids that are too warm, especially when delivered with shorter tubes, because the fluids don't have time to cool down enough after exiting the warming devices.

SUMMARY

The present invention solves the above-described problems and provides a distinct advance in the art of warming devices for IV fluids, feeding fluids, and other fluids delivered to patients. More particularly, the invention provides a heated patient tube assembly that gradually warms fluids to a desired temperature as the fluids flow through a tube and maintains the desired temperature until the fluids are delivered to a patient without the above-described temperature drop and overheating problems.

A heated patient tube assembly constructed in accordance with an embodiment of the present invention broadly comprises an elongated hollow tube for carrying fluids to a patient; a heating assembly at least partially embedded within the tube for heating the tube and fluids carried in the tube; and a control assembly for controlling the heating assembly such that the fluids exit the tube at a desired and consistent temperature.

The tube may be an intravenous (IV) tube, an enteral feeding tube, a blood transfusion tube, and/or any other device configured to carry IV fluids, milk, feeding formulas, blood, and/or any other fluids to infants, elderly person, or any other patients or persons. The tube may be any length, and in one embodiment, has an increased wall thickness to accommodate the heating assembly as described below.

The heating assembly heats fluids carried in the tube as they are delivered to a patient and comprises a heating element and a connector. In accordance with an important aspect of the invention, the heating element is embedded in the tube substantially between the tube's inner and outer walls. The heating element produces resistive-type heat when subjected to an electrical current or electromagnetic wave to warm the tube and may be a metal wire, filament, flexible ceramic strip, etched foil heater, silicon particle, or any other element that generates heat.

The heating element may extend parallel to the inner fluid passageway of the tube or may wrap around the fluid passageway in some pattern. In one embodiment, the heating element is wound around the interior fluid passageway of the tube in a helical pattern. The pitch of the helical pattern may be uniform across the entire length of the tube or may increase from the first open end of the tube toward the second open end of the tube such that the heating capacity of the heating element is greatest at the beginning of the tube. This ensures that fluids are quickly and uniformly heated as they enter the tube but not overheated as they exit the tube. In some embodiments, the heating element terminates a distance from the second open end of the tube so that the fluids aren't heated immediately before being discharged from the tube.

The connector is coupled with the heating element and extends at least partially from the outer wall of the tube so that it may be connected to the control assembly or other power source for powering the heating element. The connector may be a USB connector, mini USB connector, 4-pin or 16-pin connector, 120 VAC connector, 12 VDC connector, or any other connector capable of providing electricity to the heating element. In some embodiments, the connector may be omitted, and the heating element may receive power inductively or through other wireless methods.

The control assembly controls operation of the heating element so as to heat fluids carried in the tube to a desired and consistent temperature. An embodiment of the control assembly comprises at least one temperature sensor and a controller. The control assembly, or portions thereof, may be remote from the tube or integrated into or on the tube as described below.

The temperature sensor senses a temperature of the tube, fluid carried in the tube, or the heating element itself and may be a thermistor, a thermocouple, a silicon bandgap temperature sensor, or any other temperature sensor. The temperature sensor may be positioned anywhere on, in, or near the tube. In one embodiment, the temperature sensor is integrated with the heating element for obtaining a more accurate temperature reading. Alternatively, the temperature sensor may be integrated with the controller such that the temperature is obtained as a function of a voltage drop across the heating element, a current draw across the heating element, or any other suitable electronic property. In embodiments which the temperature sensor and controller are mounted apart, the temperature sensor may be coupled with the controller via the connector or may wirelessly send data to the controller.

The controller is coupled with the temperature sensor and the heating element and is operable to control a temperature of the heating element in response to the temperature sensor. The controller may be integrated in the tube or mounted remotely from the tube. For example, the controller may be mounted remotely from the tube in its own enclosure and connected to the heating element via the connector or may be wired to a cable between the connector and the heating assembly such that the connector only connects to a power source. In another embodiment, the controller may be attached to or embedded in the tube along with the temperature sensor.

In use, the first end of the tube is connected to a pump or other fluid source, the second end of the tube is provided to a patient, and the connector is coupled with the control assembly or another power source. The heating element then begins to warm the fluid-carrying tube and fluids carried by the tube while the fluids are being delivered to a patient.

The controller maintains the temperature of the fluids passing through the tube between approximately 90° F. (32° C.) and 103° F. (39° C.). Temperatures within this range are ideal for fluid adsorption and digestion. When the controller determines via the temperature sensor that the fluid temperature is above an upper threshold temperature, it temporarily deactivates or reduces the output of the heating element until the temperature has dropped below the upper threshold temperature.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein:

FIG. 1 is a perspective view of a heated patient tube assembly constructed in accordance with an embodiment of the invention with portions of the assembly shown in partial section to reveal internal components;

FIG. 2 is a vertical sectional view of the heated patient tube assembly taken along line 2-2 of FIG. 1;

FIG. 3 is a perspective view of a heated patient tube assembly constructed in accordance with another embodiment of the invention with portions of the assembly shown in partial section to reveal internal components;

FIG. 7 is a perspective view of an embodiment of the heated patient tube assembly with an integrated control assembly;

FIG. 8 is an enlarged perspective view of the control assembly of FIG. 7.

Figure 4:
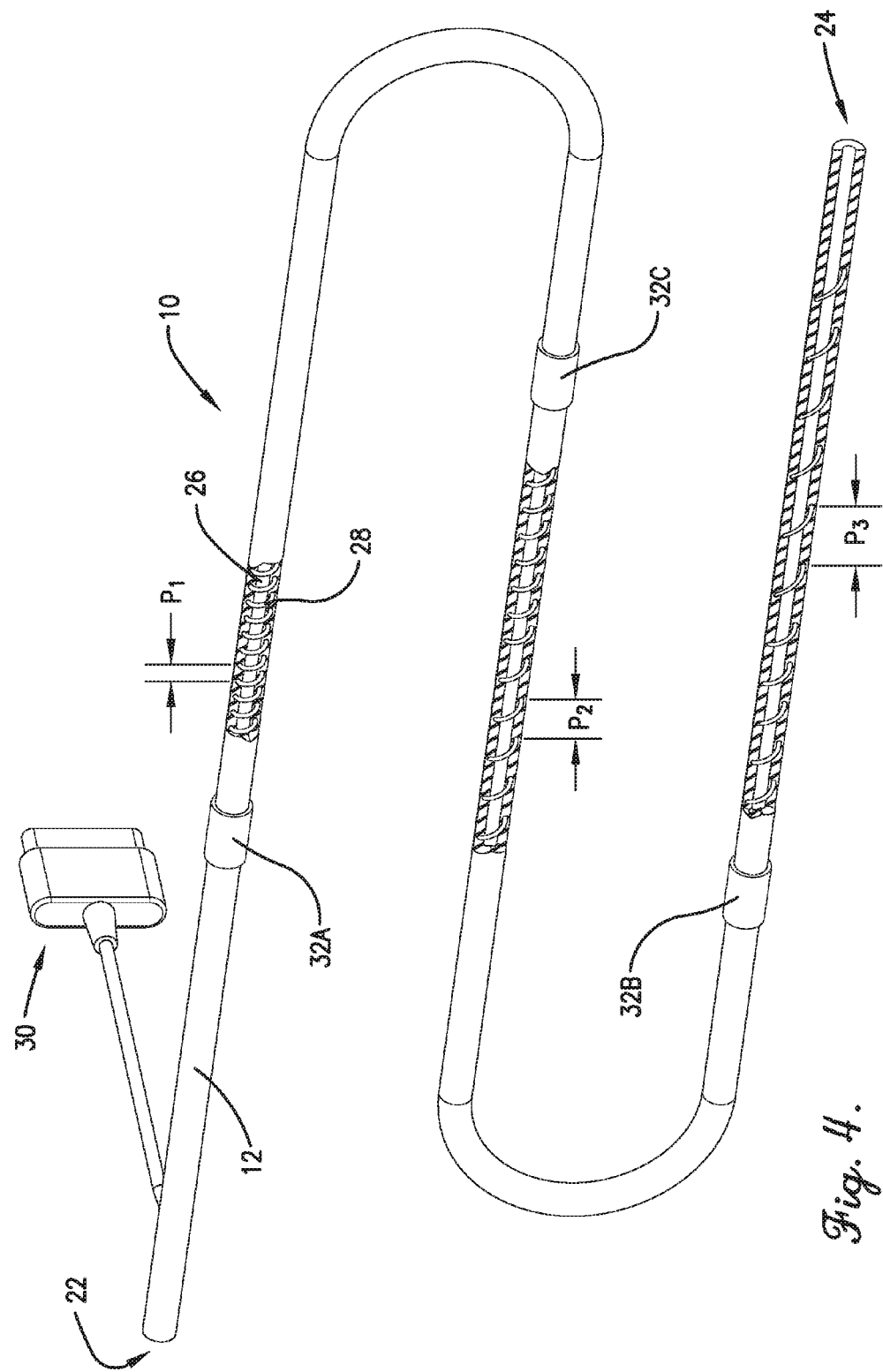
FIG. 4 is a perspective view of a heated patient tube assembly constructed in accordance with yet another embodiment of the invention with portions of the assembly shown in partial section to reveal internal components.

The drawing figures do not limit the invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 6:
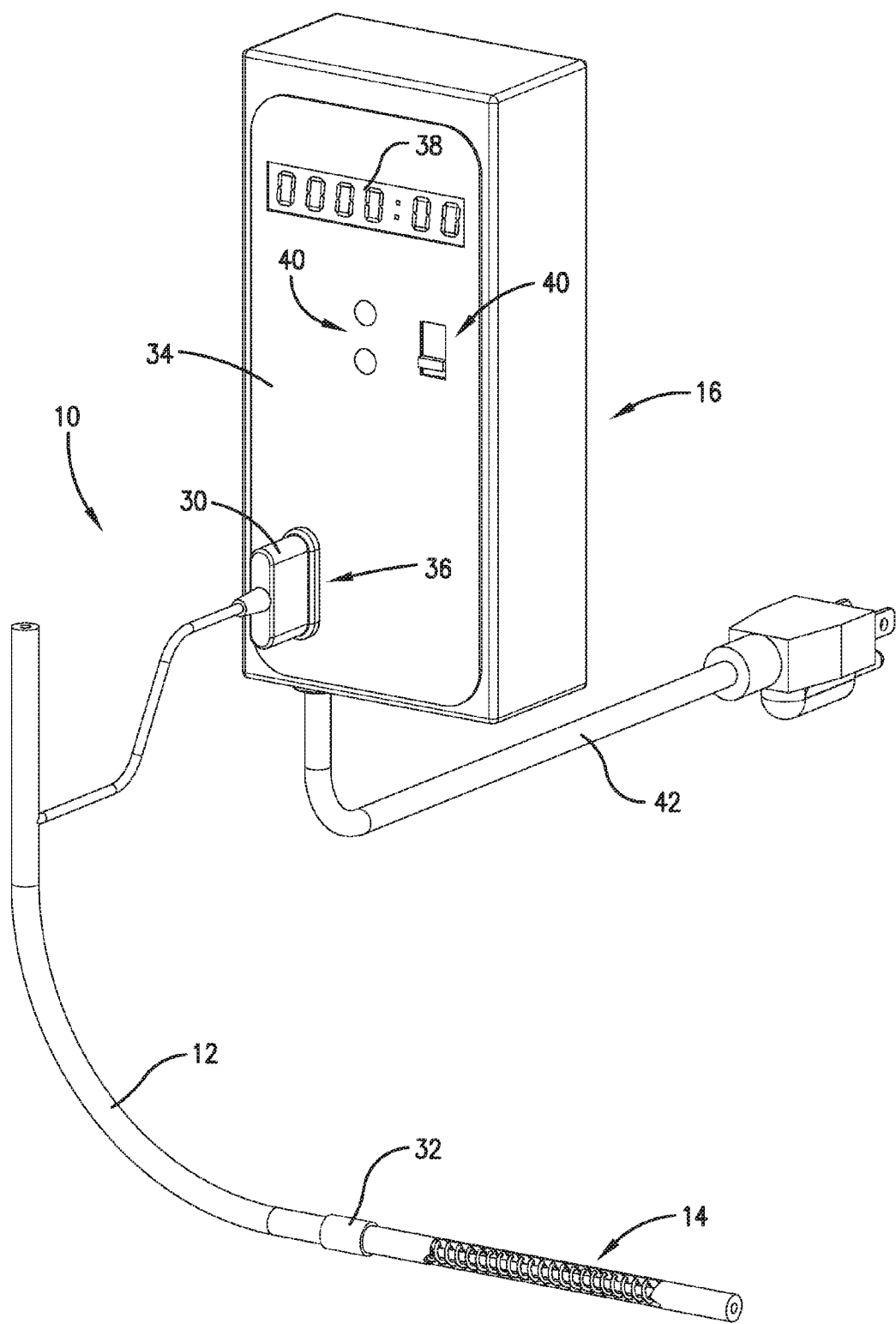
FIG. 6 is a perspective view of an embodiment of the heated patient tube assembly shown coupled with an external control assembly.

Turning now to the drawing figures, and initially FIGS. 1 and 6, a heated patient tube assembly 10 constructed in accordance with an embodiment of the invention is illustrated. The patient tube assembly 10 broadly comprises an elongated hollow tube 12 for carrying fluids to a patient; a heating assembly 14 at least partially embedded within the tube for heating the tube and fluids carried in the tube; and a control assembly 16 for controlling the heating assembly 14 so as to heat fluids carried in the tube to a desired and consistent temperature.

The tube 12 may be configured for use as an intravenous (IV) tube, an enteral feeding tube, a blood transfusion tube, and/or any other device for carrying IV fluids, milk, feeding formulas, blood, and/or any other fluids to infants, elderly person, or any other patients or persons. As best shown in FIGS. 1 and 2, the tube 12 has an inner wall 18, an outer wall 20, and first and second open ends 22, 24, with the inner wall 18 defining an interior fluid passageway 26 for carrying fluids. The first open end 22 receives fluids from a pump, bag, or other fluid source and the second open end 24 delivers the fluids to a patient, or vice versa. The tube 12 may have any length and diameter and is preferably constructed of medical grade rubber, plastic, or similar flexible materials.

Because the heating assembly 14 is at least partially embedded within the tube 12 as described in more detail below, the tube 12 is thicker than many conventional IV tubes, enteral feeding tubes, and blood transfusion tubes. An embodiment of the tube has an inside diameter of 2-4 mm; an outside diameter of 3-6, and a wall thickness of ¼-1 mm.

The heating assembly 14 is at least partially embedded within the tube 12 so as to heat fluids carried in the tube 12 as they are delivered to a patient. Importantly, the heating assembly 14 doesn't just heat a small portion of the tube, but instead heats and maintains the temperature of the fluids along nearly the entire length of the tube.

An embodiment of the heating assembly 14 comprises a heating element 28 and a connector 30. The heating element 28 is embedded in the tube 12 substantially between the tube's inner and outer walls 18, 20. The heating element 28 produces resistive-type heat when subjected to an electrical current or electromagnetic wave and may be a metal wire (e.g., a Nichrome wire), a metal filament, flexible ceramic strip, etched foil heater, or any other element that generates heat. The heating element 28 may even be silicone particles or other particles embedded in the tubing that are heated when exposed to electricity and/or when placed in the presence of an electromagnetic wave. Some embodiments of the heating element 28 may include a heat conductive layer such as teflon, kapton, silicone, or felt and an overlying insulating layer for protecting the heating element and guiding heat from the heating element to fluids carried in the fluid-carrying tube.

The heating element 28 may extend parallel to the tube's interior fluid passageway 26 in a relatively straight line or may encircle the interior fluid passageway in some pattern. In one embodiment, the heating element is wound around the interior fluid passageway 26 in a helical pattern with a pitch P as shown in FIG. 1. The pitch P may be selected to provide any desired amount of heating. For example, a relatively tight or small pitch P may be selected to provide relatively higher heating and a relatively looser or larger pitch P may be selected to provide relatively less heating. In one embodiment, the pitch P is between 1/8"-1".

The pitch P of the heating element 18 may be uniform across the length of the tube as depicted in FIG. 1 or may vary from one end of the tube to the other as depicted in FIGS. 3 and 4. For example, as illustrated in FIG. 3, the pitch P may increase from the first open end 22 of the tube toward the second open end 24 of the tube, with a $P_1$ of 1/8"-1/4", a $P_2$ of 1/4"-1/2", and a $P_3$ of 1/2"-1". This ensures fluids are quickly and uniformly heated as they enter the tube 12 but not overheated before they exit the tube. In another embodiment illustrated in FIG. 4, the heating element 28 has the same increasing pitch as the FIG. 3 embodiment, but the heating element 28 terminates a distance from the second open end of the tube 24 so that the fluids are not heated immediately before they exit the tube. The heating element 28 may terminate any distance from the second end 24 of the tube, and in one embodiment, terminates 1"-3" before the second end 24.

Figure 5:
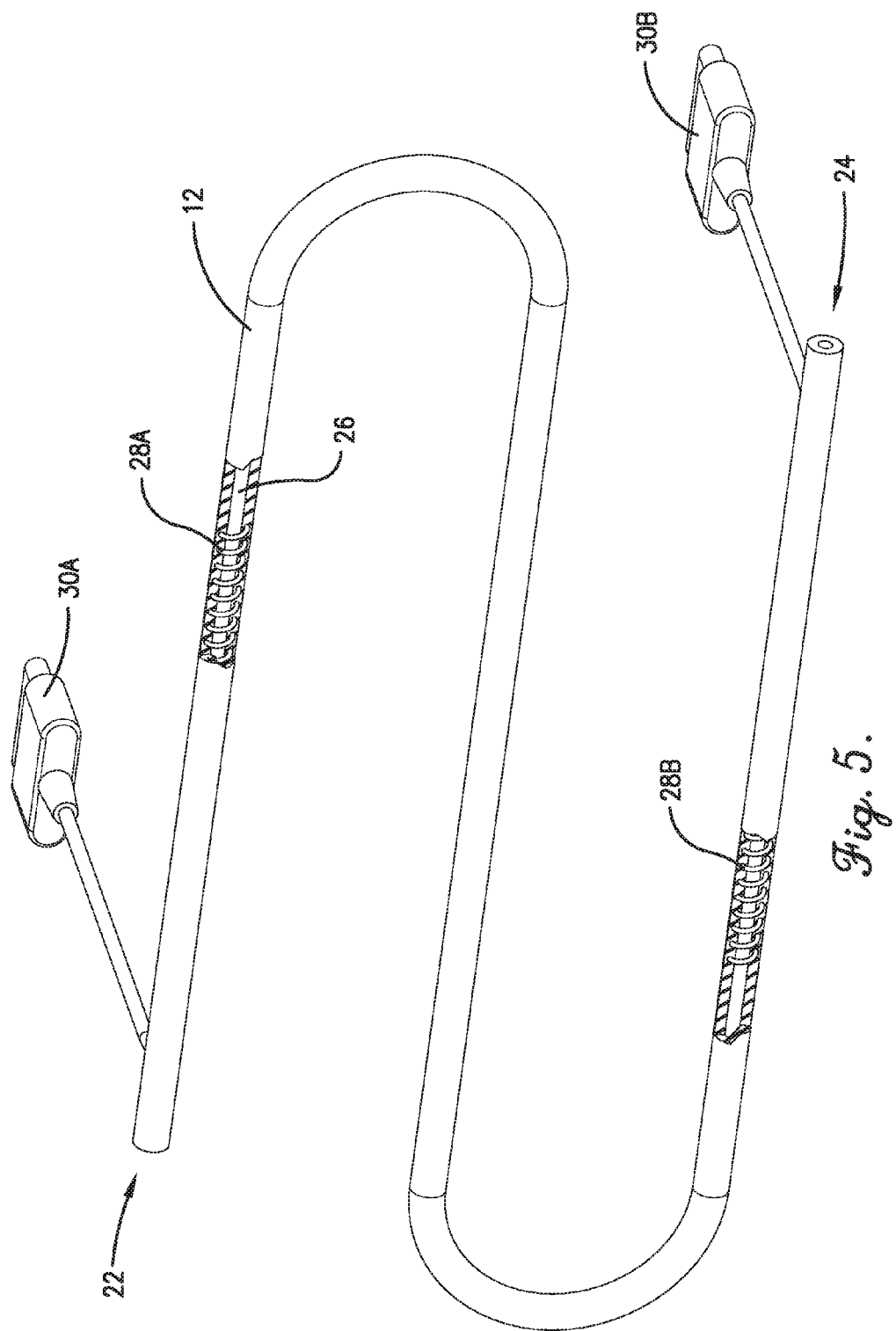
FIG. 5 is a perspective view of a heated patient tube assembly constructed in accordance with yet another embodiment of the invention with portions of the assembly shown in partial section to reveal internal components.

In another embodiment of the invention, more than one heating element may be embedded in a single piece of tube. For example, as illustrated in FIG. 5, a first heating element 28A may be embedded in the tube 12 near its first open end 22 and a second heating element 28B may be embedded in the tube near its second open end 24. This embodiment heats fluids as they first enter the tube 12 and then heats the fluids again, if necessary, as they exit the tube. The control assembly described below may provide different amounts of power to the heating elements 28A, 28B, so as to provide different levels of heating. For example, the control assembly may provide more power to the first heating element 28A so as to quickly warm a refrigerated fluid and less power to the heating element 28B so as to maintain the fluid temperature without overheating the fluid. Each heating element may have its own connector 30A, 30B, or the heating elements may share a single connector.

Returning to FIG. 1, an embodiment of the connector 30 extends at least partially from the outer wall 20 of the tube so that it may be connected to the control assembly 16 or directly to a power source for powering the heating element 28. The connector may be a USB connector, mini USB connector, 4-pin or 16-pin connector, 120 VAC connector, 12 VDC connector, or any other connector capable of providing electricity to the heating element 28. In some embodiments, the connector 30 may be omitted, and the heating element 28 may receive power inductively or through other wireless methods. The connector 30 may include separate electrical contacts, one of more for delivering electricity to the heating element 18 and one or more for receiving temperature data from a temperature sensor described below. Alternatively, separate connectors may be used for powering the heating element 18, delivering data from the temperature sensor 14 to the control unit 16, and controlling other components.

The control assembly 16 controls operation of the heating element 28 such that fluids exit the tube 12 at a desired and consistent temperature. The control assembly 16 may be a stand-alone component that provides power to the heating element via the connector 30 as shown in FIG. 6 or may be partially or fully integrated into the tube 12 as shown in FIG. 7. An embodiment of the control assembly comprises at least one temperature sensor 32 and a controller 34.

The temperature sensor 32 senses a temperature of the tube 12, the fluid in the tube, and/or the heating element 28 and may be a thermistor, a thermocouple, a silicon bandgap temperature sensor, or any other temperature sensor. The temperature sensor may be mounted on the tube as shown in FIG. 1, embedded in the tube substantially between the tube's inner and outer walls, integrated in the heating element, or integrated with the controller. The temperature sensor 32 may directly sense a temperature of the tube or may calculate an estimated temperature as a function of a voltage drop across the heating element, a current draw across the heating element, or any other suitable electronic property. For embodiments of the invention in which the temperature sensor 32 and controller 34 are mounted apart, the temperature sensor 32 may provide temperature data to the controller 34 via the connector 30 or wirelessly via radio frequency signal transmissions, near frequency communication (NFC) technology, or the like.

Several temperature sensors 32 may be positioned along the length of the tube for sensing temperatures at several locations. For example, as illustrated in FIG. 3, a temperature sensor 32A may be positioned near the first end 22 of the tube, and another temperature sensor 32B may be positioned near the second end 24 of the tube 12 such that a temperature difference between the two opposite ends of the tube may be sensed and used to determine a heating level of the heating element 18. In another embodiment illustrated in FIG. 4, a sensor 30A may be placed near the first open end of the tube 22, another sensor 32B may be placed near the second open 24 end of the tube, and at least one more sensor 32C may be spaced between the other two sensors such that temperatures of the fluid may be sensed as the fluid travels through the entire length of the tube. When only one temperature sensor 32 is provided, it is preferably positioned near the second end 24 of the tube so as to sense a temperature of the fluid immediately before it is discharged from the tube.

The temperature sensor or sensors 32 described and illustrated herein may be changed without departing from the scope of the invention. For example, additional temperature sensors and/or different types of temperature sensors may be used for more accurate temperate readings and more complete data collection.

The controller 34 is coupled with the temperature sensor or sensors 32 and the heating element 28 and is operable to control a temperature or power level of the heating element 28 in response to data from the temperature sensors. The controller 34 may include any combination of control circuitry, power circuitry, controllers, processors, and/or other electronics and has internal or external memory for storing the data and the computer programs described below.

The controller 34 may be mounted anywhere. For example, in an embodiment illustrated in FIG. 6, the controller 34 may be mounted remotely from the tube in its own enclosure and connected to the heating element 28 and the sensor 32 via the connector 30. In another embodiment illustrated in FIG. 7, the controller 34 may be wired to a cable 36 between the connector 30 and the heating element 28. In this embodiment, no external control of the patient tube assembly 10 is required, such that the connector 30 only requires a power source connection. In yet another embodiment, the controller 34 may even be attached to or embedded in the tube 12 along with the temperature sensor 32. The controller 34 and temperature sensor 32 may also be configured to communicate wirelessly such as via radio frequency signal transmissions, near frequency communication (NFC) technology, or the like.

The controller 34 may implement aspects of the invention with one or more computer programs stored in or on computer-readable medium residing on or accessible by the controller. Each computer program preferably comprises an ordered listing of executable instructions for implementing logical functions in the controller. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

Embodiments of the controller 34 that are remote from the tube 12 may further include a port 36 for connecting to the connector 30 extending from the tube, a display 38, a number of user inputs 40, and a power source 42, all of which may be contained within or on a housing as shown in FIG. 6. More details of such a controller are described in more detail in U.S. patent application Ser. No. 15/282,612, FLUID WARMING DEVICE, filed Sep. 30, 2016, hereby incorporated by reference into the present application in its entirety. When the controller 34 is directly connected to the heated patient tube assembly 10 as shown in FIGS. 7 and 8, it may include simple pushbuttons for adjusting its power level and a small display for displaying a target and/or actual temperature.

The above-described heated patient tube assembly 10 may be used as follows. The first end 22 of the tube 12 is connected to a pump or other fluid source, and the opposite second end 24 of the tube is connected or otherwise provided to a patient. The connector 30 extending from the tube 12 is then coupled with the control assembly 16 or another power source. The pump draws fluid from the fluid source and may force it through the tube 12 at a flow rate of approximately 0.25 ml/min to approximately 1 ml/min. The fluid may also be gravity fed. The heating element 28 warms the tube 12 and fluids as the fluids pass through the tube.

The controller 34 maintains the temperature of the fluids within the tube between approximately 90° F. (32° C.) and 103° F. (39° C.). When the controller 34 determines via the temperature sensor 32 that the fluid-carrying tube or the fluids therein are above 103° F. (39° C.) or any other selected upper limit temperature, the controller 34 temporarily deactivates or reduces the output of the heating element 28 until the temperature has dropped to another predetermined temperature between 90° F. (32° C.) and 103° F. (39° C.). The controller 34 reactivates or increases the power of the heating element 28 when the temperature of the tube 12 drops to the predetermined lower threshold temperature or when the temperature of the tube drops to an intermediate temperature. This ensures that the temperature of the fluid exiting the tube 12 is within the TNZ or another desired temperature range.

The controller 34 may maintain the temperature of the fluids in the tube 12 by frequently activating and deactivating the heating element 28 when the temperature of the tube reaches these temperatures. This allows the temperature of the tube, and hence the temperature of the fluid being delivered into the patient's vein, stomach, or intestine, to remain relatively constant during operation instead of rising and falling between the upper and lower threshold temperatures of the TNZ.

The patient tube assembly 10 may also comprise an overheat sensor for sensing an overheating condition for preventing the heating element 28 from warming the tube 12 to a temperature above an upper limit of the TNZ or another predetermined temperature. The overheat sensor may also prevent the heating element 28 from damaging its heat conductive layer and/or the insulating sheath. The overheat sensor may be positioned near a midpoint of the heating element so as to ensure that overheating is detected as early as possible. The overheat sensor may comprise a single sensor that shuts off or turns down the heating element once the tube reaches a particular temperature or it may comprise several sensors that form a redundant multi-stage sensor assembly that that shuts off or turns down the heating element at several successive temperatures. The multi-stage sensor assembly provides redundant temperature protection in case any of the sensors fail.

At any time, the overheat sensor may generate a signal representative of an overheating condition. The overheating condition may be a temperature near or at an upper level of the TNZ or another predetermined maximum allowed fluid temperature. The overheating condition may also be a maximum allowed temperature of the temperature sensors, ceramic felt layer, or insulating sheath. The controller 34 will then turn off or decrease a heat level of the heating element 28. The controller 34 may then turn on or increase the heat level of the heating element if the overheat sensor no longer senses an overheat condition.

One or more of the above-described steps may be performed in a different order than described or simultaneously. For example, the heating element 28 may be turned on before the fluid-carrying tube is connected to a pump or other source of fluid.

The above-described patient tube assembly provides several advantages over conventional fluid warming devices. For example, the assembly gradually warms fluid as it is being delivered to a patient and maintains the temperature of the fluid until it is discharged from the assembly.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A heated patient tube assembly comprising:
an elongated hollow tube having an inner wall, an outer wall, and first and second open ends, the inner wall defining an interior fluid passageway for carrying fluids from a fluid source to a patient;

a heating assembly for heating the fluids as they pass through the interior fluid passageway, the heating assembly comprising:

a first heating element embedded in the tube substantially between the inner and outer walls near the first open end, a second heating element embedded in the tube substantially between the inner and outer walls so that the second heating element is near the second open end spaced from the first heating element, and a connector coupled with the heating elements and extending at least partially from the outer wall of the tube so that the connector may be connected to a power source for powering the heating elements; and a control assembly for controlling the heating assembly such that the fluids exit the tube at a desired and consistent temperature, the control assembly comprising a temperature sensor for sensing a temperature of the fluids carried by the tube, the temperature sensor being attached to the tube or embedded in the tube substantially between the inner and outer walls, the control assembly being configured to provide a first amount of power to the first heating element for quickly warming the fluids to the desired temperature after the fluids enter the first open end of the tube and a second amount of power less than the first amount of power to the second heating element for maintaining the fluids at the desired temperature without overheating the fluids.

2. The heated patient tube assembly of claim 1, the control assembly further comprising a controller coupled with the temperature sensor and the heating elements and operable to control a heating level of each heating element in response to the temperature sensor.

3. The heated patient tube assembly of claim 2, wherein the controller is remote from the tube and receives data from the temperature sensor via the connector.

4. The heated patient tube assembly of claim 1, wherein the heating elements are wound around the interior fluid passageway in a helical pattern.

5. The heated patient tube assembly of claim 4, wherein a pitch of each helical pattern increases from the direction of the first open end of the tube toward the second open end of the tube.

6. The heated patient tube assembly of claim 4, wherein the second heating element terminates a distance from the second open end of the tube.

7. A heated patient tube assembly for carrying fluids to a patient, the heated patient tube assembly comprising:

an elongated hollow tube having an inner wall, an outer wall, and first and second open ends, the inner wall defining an interior fluid passageway for carrying fluids from a fluid source to the patient;

a heating assembly for heating the fluids before they are delivered to the patient, the heating assembly comprising:

a first heating element embedded in the tube substantially between the inner and outer walls near the first open end and wound around the interior fluid passageway in a helical pattern, a second heating element embedded in the tube substantially between the inner and outer walls so that the second heating element is near the second open end spaced from the first heating element and wound around the interior fluid passageway in a helical pattern, and a connector coupled with the heating elements and extending at least partially from the outer wall of the tube so that the connector may be connected to a power source for powering the heating elements; and a control assembly for controlling the heating assembly such that the fluids exit the tube at a desired and consistent temperature, the control assembly comprising:

a first temperature sensor embedded in the tube substantially between the inner and outer walls near the first open end for sensing a temperature of the fluids shortly after the fluids have entered the tube at the first open end, a second temperature sensor embedded in the tube substantially between the inner and outer walls near the second open end for sensing a temperature of the fluids shortly before the fluids exit the tube at the second open end, and a controller coupled with the temperature sensors and the heating elements, the controller being configured to determine a heating level of each heating element based on a difference between the temperature sensed at the first temperature sensor and the temperature sensed at the second temperature sensor and operable to control the heating levels of the heating elements by providing a first amount of power to the first heating element for quickly warming the fluids to the desired temperature after the fluids enter the first open end of the tube and a second amount of power less than the first amount of power to the second heating element for maintaining the fluids at the desired temperature without overheating the fluids, wherein the controller is remote from the tube and receives data from the temperature sensors via the connector or wireless transmission.

8. The heated patient tube assembly of claim 1, wherein the control assembly further comprises a third temperature sensor spaced between the first temperature sensor and the second temperature sensor for sensing a temperature of the fluids as the fluids travel through a middle portion of the tube.

* * * * *